United States Patent
Brennan

(10) Patent No.: US 6,326,496 B1
(45) Date of Patent: Dec. 4, 2001

(54) PROCESS FOR PREPARING AN INTERMEDIATE IN THE PRODUCTION OF PAROXETINE

(75) Inventor: James Patrick Brennan, Nottingham (GB)

(73) Assignee: Knoll Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/423,749

(22) PCT Filed: May 13, 1998

(86) PCT No.: PCT/EP98/02826

§ 371 Date: Nov. 15, 1999

§ 102(e) Date: Nov. 15, 1999

(87) PCT Pub. No.: WO98/52920

PCT Pub. Date: Nov. 26, 1998

(30) Foreign Application Priority Data

May 17, 1997 (GB) .................................... 9710004

(51) Int. Cl.$^7$ ..................... C07D 211/22; C07D 405/12; C07D 211/58
(52) U.S. Cl. ............................ 546/240; 546/197
(58) Field of Search ..................... 546/240, 197

(56) References Cited

U.S. PATENT DOCUMENTS

| | | | |
|---|---|---|---|
| 3,849,542 | 11/1974 | Snover et al. | 423/644 |
| 4,007,196 | 2/1977 | Christensen et al. | 260/293 |
| 4,902,801 | * 2/1990 | Faruk et al. | 546/220 |
| 5,091,393 | * 2/1992 | Hartog et al. | 514/317 |
| 5,258,517 | * 11/1993 | Zepp et al. | 546/240 |
| 5,489,599 | * 2/1996 | Carter et al. | 514/317 |
| 5,681,962 | * 10/1997 | Callander | 546/219 |
| 5,948,914 | * 9/1999 | Sugi et al. | 546/240 |
| 6,153,755 | * 11/2000 | Ennis et al. | 546/240 |

FOREIGN PATENT DOCUMENTS

| | | |
|---|---|---|
| WO 96/36636 | 11/1996 | (WO) . |
| WO 98/01424 | 1/1998 | (WO) . |

OTHER PUBLICATIONS

Willocks et al., "The synthesis of [$^{14}$C]–3S, 4R–4–(4–fluorophenyl)–3–(3,4—methylenedioxyphenoxymethyl) piperidine hydrochloride (BRL 29060A), and mechanistic studies using carbon–13 labeling", Journal of Laabelled Compounds & Radiopharmeceuticals, vol. XXXIII No. 8, pp. 783–794(1993).

* cited by examiner

Primary Examiner—Floyd D. Higel
(74) Attorney, Agent, or Firm—Keil & Weinkauf

(57) ABSTRACT

A process for the preparation of a compound of formula I

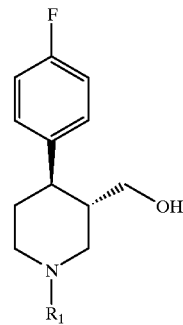

in which $R_1$ represents an amine protecting group wherein a compound of formula II

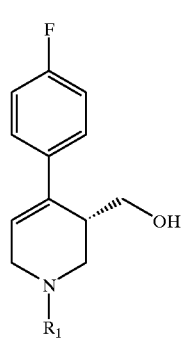

in which $R_1$ is as defined above is reduced by a metal hydride in the presence of an inorganic salt in the presence of a diluent.

10 Claims, No Drawings

PROCESS FOR PREPARING AN INTERMEDIATE IN THE PRODUCTION OF PAROXETINE

This invention relates to a process for the preparation of (−)-trans-1-benzyl-3-hydroxymethyl-4-(4-fluorophenyl)piperidine which is a useful intermediate in the preparation of paroxetine.

U.S. Pat. No. 4,007,196 discloses compounds which possess anti-depressant activity. One particular compound disclosed in this patent is known as paroxetine and has the structure A below:

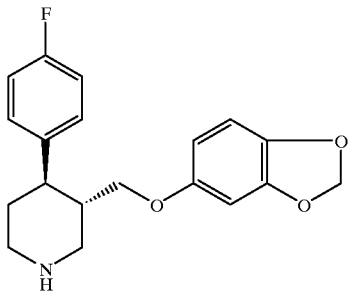

This compound has been found to be especially useful in the treatment of depression and several processes have been described to prepare this important compound.

WO 96/36636 (which is incorporated herein by reference) discloses one such process. Step C in claim 1 of this application describes the reduction of a compound of formula B

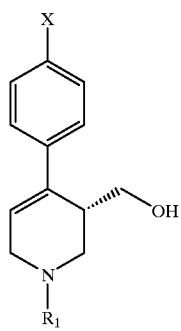

to give a compound of formula C

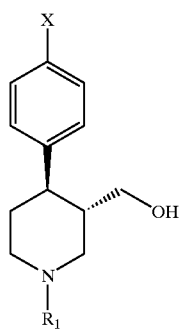

in which X is halogen, preferably F, and $R_1$ is $C_{2-5}$ alkyl, phenyl $C_{1-5}$ alkyl or substituted phenyl $C_{1-5}$ alkyl. The reduction is carried out using a metal hydride which is preferably, according to claim 4, $LiAlH_4$ or $NaAlH_4$. The only example given in the application relates to a compound of formula B, in which X is F and $R_1$ is ethyl, which was reduced using a mixture of sodium hydride and lithium aluminium hydride.

When this reaction is carried out, following the conditions described in WO96/36636, in the case where X is F and $R_1$ is benzyl, it has been found that unacceptable levels of defluorination occur. This impurity is difficult to separate from the desired compound at this stage and results in the presence of the desfluoro analogue of paroxetine in the final compound. Once again it is difficult to separate the desfluoro analogue of paroxetine from paroxetine. This results in time consuming separation processes which are wasteful of material and costly.

Surprisingly a process has been found in which a minimal amount of defluorination occurs during the reduction stage. The present invention provides a process for the preparation of a compound of formula I

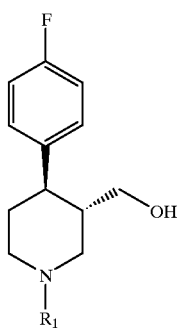

in which $R_1$ represents an amine protecting group wherein a compound of formula II

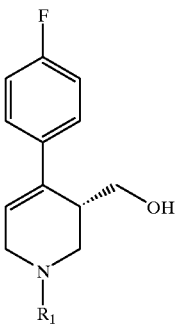

in which $R_1$ is as defined above is reduced by a metal hydride in the presence of an inorganic salt in the presence of a diluent.

Suitably the amine protecting group is one which is inert to reduction by a metal hydride Preferably the amine protecting group is selected from a) allyl, b) benzhydryl, c) methoxymethyl, d) benzyloxymethyl, e) tetrahydropyranyl, f) an optionally substituted benzyl group, g) di(p-methoxyphenyl)methyl, h) triphenylmethyl, i) (p-methoxyphenyl)diphenylmethyl, j) diphenyl-4-pyridylmethyl, k) 2,4,6-trimethylbenzenesulphonyl, l) toluenesulphonyl, m) benzylsulphonyl, n) a $C_{1-6}$ alkyl group, o) a trifluoro $C_{1-4}$ alkyl group, p) an alkynyl group or q) p-methoxybenzyl or optionally substituted ammonium.

More preferably the amine protecting group is a benzyl group which is optionally substituted on the phenyl ring by one or more of the following groups: a $C_{1-4}$ alkyl group, a $C_{1-4}$ alkoxy group, halo or nitro. Most preferably $R_1$ represents benzyl.

Suitably the metal hydride is sodium hydride, potassium hydride, magnesium hydride, calcium hydride, sodium borohydride, potassium borohydride, lithium borohydride, lithium aluminium hydride, sodium aluminium hydride, aluminium hydride, sodium bis-(2-methoxyethoxy) aluminium hydride, a lithium mono($C_{1-4}$ alkoxy)aluminium hydride, a lithium di($C_{1-4}$ alkoxy)aluminium hydride or sodium diethylaluminium hydride or mixtures thereof. Preferably the metal hydride is lithium aluminium hydride or sodium aluminium hydride. More preferably the metal hydride is lithium aluminium hydride.

Suitably the amount of metal hydride used is in the range of 0.5–5 molar equivalents with respect to the amount of compound of formula If used. Preferably the amount of metal hydride used is in the range of 0.75–1.25 molar equivalents. More preferably, the amount of metal hydride used is in the range of 0.90–1.10 molar equivalents.

Suitably the inorganic salt is a salt of lithium, sodium, magnesium, calcium, zinc, lanthanum or iron, or mixtures thereof. Preferably the inorganic salt is a halide salt of lithium, sodium, calcium, zinc, magnesium, lanthanum or iron or mixtures thereof. More preferably the inorganic salt is selected from lithium chloride, sodium chloride, calcium chloride, zinc chloride, iron (II) chloride, iron (III) chloride, lanthanum chloride, magnesium chloride, magnesium fluoride, magnesium bromide or magnesium iodide or mixtures thereof. Most preferably the inorganic salt is magnesium chloride, magnesium bromide or magnesium iodide. An especially preferred salt is magnesium chloride.

The mechanism for this process has not been investigated in detail. It will be appreciated by those skilled in the art that the active reducing agent may be formed by a reaction between the metal hydride initially employed and the inorganic salt. For example, in the case of lithium aluminium hydride and magnesium chloride the active species may be one or more of magnesium hydride, chloromagnesium aluminium hydride, magnesium aluminium hydride or lithium magnesium aluminium hydride or a complex of magnesium chloride and lithium aluminium hydride. It is to be understood that this process covers all such equivalents.

Suitably the amount of inorganic salt used is in the range of 0.25 molar equivalents to 5 molar equivalents with respect to the amount of the compound of formula It used. Preferably the amount of inorganic salt used is in the range of 0.5–1.5. More preferably the amount of inorganic salt used is in the range of 0.75–1.25 molar equivalents with respect to the amount of the compound of formula II used.

Suitably the diluent is an organic liquid which is inert to the metal hydride employed and is preferably a solvent for the compound of formula II. Preferably the diluent is an ether or a hydrocarbon or a mixture thereof. More preferably the diluent is selected from tetrahydrofuran, toluene, dioxane, diethyl ether, diisopropyl ether, t-butylmethyl ether, diglyme, ethylene glycol dimethyl ether or mixtures thereof. Most preferably the diluent is tetrahydrofuran.

Suitably the amount of the diluent is in the range of 1 part by weight to 100 parts by weight with respect to the compound of formula II employed. Preferably the amount of the diluent is in the range of 2 parts by weight to 50 parts by weight with respect to the compound of formula II employed. More preferably the amount of the diluent is in the range of 3 parts by weight to 10 parts by weight with respect to the compound of formula II employed.

Suitably the process is carried out at a temperature in the range of $-70°$ C. to the boiling point of the diluent employed. Preferably the process is carried out at a temperature in the range 0–150° C. More preferably the process is carried out at a temperature in the range 0–100° C. Most preferably the process is carried out at a temperature in the range 50–70° C.

Suitably the amount of desfluoro compound obtained is in the range of 0.001% to 1%. This percentage figure refers to the result obtained by the HPLC method described in the Examples. Preferably the amount of desfluoro compound obtained is in the range of 0.001 to 0.5%. More preferably the amount of desfluoro compound obtained is in the range of 0.001 to 0.2%.

The process of the present invention is advantageous because it provides a pure precursor to paroxetine. Paroxetine may be obtained in a pure form from compounds of formula I by a) conversion of the hydroxy group into a leaving group, for example halo or tosyloxy, b) reaction with sesamol or a salt thereof, c) removal of the protecting group $R_1$ and optionally d) salt formation, for example the hydrochloride salt as the anhydrous form or the hemihydrate.

The invention is illustrated by the following Examples which are given by way of example only. The final product of each of these Examples was characterised by one or more of the following procedures: gas-liquid chromatography; high performance liquid chromatography; elemental analysis; nuclear magnetic resonance spectroscopy and infrared spectroscopy.

The desfluoro compound is (−)-trans-1-benzyl-3-hydroxymethyl-4-phenylpiperidine.

EXAMPLES

Example 1

(−)-trans-1-benzyl-3-hydroxymethyl-4-(4-fluorophenyl)piperidine

Lithium aluminium hydride in THF (2.0 ml of a 1M solution) was carefully added to substantially anhydrous magnesium chloride (0.19 g, 1.5% $H_2O$) under nitrogen. The mixture was stirred and heated to 50° C. and then a solution of (+)-1-benzyl-3-hydroxymethyl-4-(4-fluorophenyl)-1,2,3,6-tetrahydropyridine (0.60 g, preparation given in WO96136636) in THF (1.7 ml) was added dropwise over approximately 2 minutes. The reaction mixture was stirred and boiled under reflux for 4.2 hours. The mixture was cooled to ambient temperature and then stirred in an ice/water bath whilst water (0.1 ml) then 5M sodium hydroxide solution (0.1 ml) and water (0.1 ml) were added. The suspension was diluted with THF (5 ml) and the mixture filtered. The residue was washed with THF (3×5 ml) and the combined filtrate and washings were evaporated under reduced pressure to give a yellow oil (0.49 g). This oil was analysed by GLC, Chiral HPLC and $^1H$ nmr.

GLC Conditions

Column: DB1 1.5 μm 15 m×0.53 mm

Carrier gas (B) Flow: 4.5 mis/min. Initial temp: 40° C. for 1 min.

Ramp 5° C./min to 300° C. for 7 mins.

HPLC Conditions

Column: 15 cm long, 4.6 mm internal diameter comprising particles of silica, the surface of which has been modified by chemically bonded octylsilyl groups; particle size=5 μm, Column Temperature 35° C.

Detection wavelength: 214 nm.

Mobile phase: 15% v/v acetonitrile, 0.1% v/v orthophosphoric, acid (SG 1.69) and 0.1% w/v sodium butane sulphonate in water.

The product was 98.7% pure by normalisation and contained 0.3% of the desfluoro compound by HPLC.

Example 2

(−)-trans-1-benzyl-3-hydroxymethyl-4-(4-fluorophenyl)piperidine

Lithium aluminium hydride in THF (16.7 ml of a 1M solution) was carefully added to substantially anhydrous magnesium chloride (1.58 g, 1.5% $H_2O$) under nitrogen. The mixture was stirred and heated to 50° C. and then a solution of (+)-1-hydroxymethyl-4-(4-fluorophenyl)-1,2,3,6-tetrahydropyridine (5.0 g) in THF (14.2 ml) was added dropwise over approximately 5 minutes. The reaction mixture was stirred and boiled under reflux for 6 hours. The mixture was cooled to ambient temperature and then stirred in an ice/water bath whilst water (0.8 ml) then 5M sodium hydroxide solution (0.8 ml) and water (0.8 ml) were added. The suspension was diluted with THF (5 ml) and the mixture filtered. The residue was washed with THF (3×10 ml) and the combined filtrate and washings were evaporated under reduced pressure to give a yellow oil (3.3 g). This oil was analysed by GLC, Chiral HPLC and $^1H$ nmr using the conditions described above. The product was 97.0% pure by normalisation and contained 0.2% of the desfluoro compound by HPLC.

Examples 3 to 8

Examples 3–8 were carried out in a similar manner to Example 1 using the described in Table 1. In Table 1 the following abbreviations are used: M equiv II represents molar equivalents with respect to the amount of the compound of formula II employed;
GLC=gas liquid chromatography;
HPLC=high performance liquid chromatography;
%(-F)=% of desfluoro compound;

The figures in these columns refer to percentage by normalisation.

TABLE 1

| EXAMPLE NO. | II g | THF ml | $LiAlH_4$ M equiv II | $MgCl_2$ M equiv II | Time h | % II GLC | % (-F) HPLC |
|---|---|---|---|---|---|---|---|
| 3 | 0.60 | 1.7 | 1.0 | 0.5 | 3 | 0.1 | 0.3 |
| 4 | 2.56 | 5.12 | 0.9 | 1.0 | 4 | 0 | 0.2 |
| 5 | 0.48 | 1.0 | 0.75 | 1.0 | 5 | 2.9 | 0.4 |
| 6 | 0.50 | 1.0 | 0.75 | 0.75 | 4 | 2.6 | 0.4 |
| 7 | 0.60 | 1.7 | 1.0 | 1.5 | 5 | 4.2 | 0.2 |
| 8 | 1.99 | 4.0 | 1.0 | 0.8 | 4 | 0.1 | 0.22 |

Example 9

(−)-trans-1-benzyl-3-hydroxymethyl-4-(4-fluorophenyl)piperidine

Sodium aluminium hydride in THF (2.0 ml of a 1M solution) was carefully added to substantially anhydrous magnesium chloride (0.19 g, 1.5% $H_2O$) under nitrogen. The mixture was stirred and heated to 50° C. and then a solution of (+)-1-benzyl-3-hydroxymethyl-4-(4-fluorophenyl)-1,2,3,6-tetrahydropyridine (0.60 g) in THF (1.7 ml) was added dropwise over approximately 2 minutes. The reaction mixture was stirred and boiled under reflux for 4 hours. The mixture was cooled to ambient temperature and then stirred in an ice/water bath whilst water (0.1 ml) then 5M sodium hydroxide solution (0.1 ml) and water (0.1 ml) were added. The suspension was diluted with THF (5 ml) and the mixture filtered. The residue was washed with THF (3×5 ml) and the combined filtrate and washings were evaporated under reduced pressure to give a yellow oil (0.49 g). This oil was analysed by GLC, Chiral HPLC and 1H nmr using the conditions described above. Starting material 13.2% was still present in the product as analysed by GLC. The amount of desfluoro compound as determined by HPLC was less than 0.1%.

Example 10

(−)-trans-1-benzyl-3-hydroxymethyl-4-(4-fluorophenyl)piperidine

Lithium aluminium hydride in THF (2.0 ml of a 1M solution) and toluene (0.69 ml) were carefully added simultaneously to substantially anhydrous magnesium chloride (0.53 g, 1.5% $H_2O$) under nitrogen. The mixture was stirred and heated to 50° C. and then a solution of (+)-1-benzyl-3-hydroxymethyl-4-(4-fluorophenyl)-1,2,3,6-tetrahydropyridine (2.60 g, preparable as described in WO96/36636) in THF (3.6 ml) and toluene (0.4 ml) was added dropwise over approximately 5 minutes. The reaction mixture was stirred and boiled under reflux for 3.5 hours. The mixture was cooled to ambient temperature and then stirred in an ice/water bath whilst 0. 5M sodium hydroxide solution (4.1 ml) was added. The suspension was diluted with THF (10 ml) and the mixture filtered. The residue was washed with THF (10 ml) and the combined filtrate and washings were evaporated under reduced pressure to give a yellow oil (1.83 g). This oil was analysed by GLC, Chiral HPLC and $^1H$ nmr. The title compound contained 0.24% of the desfluoro compound.

Example 11

(−)-trans-1-benzyl-3-hydroxymethyl-4-(4-fluorophenyl)piperidine

Lithium aluminium hydride in THF (3.76 ml of a 1M solution) was carefully added to substantially anhydrous magnesium bromide (0.55 g) under nitrogen. The mixture was stirred and heated to 50° C. and then a solution of (+)-1-benzyl-3-hydroxymethyl-4-(4-fluorophenyl)-1,2,3,6-tetrahydropyridine (1.12 g) in THF (2.2 ml) was added dropwise over approximately 5 minutes. The reaction mixture was stirred and boiled under reflux for 4.2 hours. The mixture was cooled to ambient temperature and then stirred in an ice/water bath whilst 0.5M sodium hydroxide solution (2 ml) and water (0.1 ml) were added. The suspension was diluted with THF (7 ml) and the mixture filtered. The residue was washed with THF (7 ml) and the combined filtrate and washings were evaporated under reduced pressure to give a yellow oil (0.99 g). This oil was analysed by GLC, Chiral HPLC and 1H nmr. The title compound contained 0.18% of the desfluoro compound.

Example 12

(−)-trans-1-benzyl-3-hydroxymethyl-4-(4-fluorophenyl)piperidine

Lithium aluminium hydride in THF (7.24 ml of a 1M solution) was carefully added to substantially anhydrous magnesium chloride (0.698 g), in THF (32 ml) with stirring under nitrogen keeping the temperature below 20° C. The mixture was stirred and heated to 50° C. and then a solution of (+)-1-benzyl-3-hydroxymethyl-4-(4-fluorophenyl)-1,2,3, 6-tetrahydropyridine (2.15 g, preparable as described in WO96/36636) in THF (3.92 ml) and toluene (2.32 ml) was added dropwise over approximately 30 minutes. The reaction mixture was stirred and boiled under reflux for 4.0 hours. The mixture was cooled to 0–5° C. in an ice/water bath whilst sodium hydroxide solution (2.48 g, 5%w/w) was added. The suspension was filtered. The residue was washed with THF (8 ml) and the combined filtrate and washings were evaporated under reduced pressure to give a yellow oil. This oil was analysed by GLC, Chiral HPLC and $^1$H nmr. The title compound contained 0.24% of the desfluoro compound.

Examples 13 & 14 were carried out in a similar manner to Example 12 but replacing magnesium chloride by a molar equivalent of the metal salt indicated as shown in Table 2.

TABLE 2

| Ex. No. | Metal Salt | Stir Time Hours | % Product GLC | % SM GLC | % Des-fluoro HPLC |
|---|---|---|---|---|---|
| 13 | MgI$_2$ | 1 | 96.4 | 0.0 | 0.13 |
| 14 | MgBr$_2$ | 1 | 97.8 | 0.55 | 0.21 |

SM = Starting material

Example 15

This example was carried out in a similar manner to Example 12 except that the toluene replaced THF as the solvent and that the mixture was heated at 110° C. with stirring for 2 hours. This procedure gave the product (93.7% pure by GLC) which contained 1.07% of the des-fluoro compound by HPLC.

Comparative Examples

In comparative reactions in which no inorganic salt was present the amount of desfluoro compound obtained was in the order of 2–4% and proved to be very difficult to remove.

What is claimed is:

1. A process for the preparation of a compound of formula I

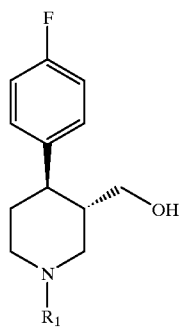

in which R$_1$ represents an amine protecting group wherein a compound of formula II

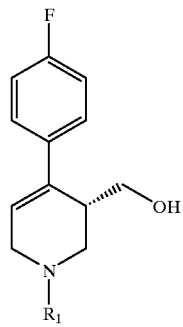

in which R$_1$ is as defined above is reduced by a metal hydride in the presence of 0.25 to 5 molar equivalents of an inorganic salt in the presence of 1 to 100 parts by weight of a diluent at a temperature of between −70° C. and the boiling point of the diluent.

2. A process according to claim 1 wherein the amine protecting group is selected from a) allyl, b) benzhydryl, c) methoxymethyl, d) benzyloxymethyl, e) tetrahydropyranyl, f) an optionally substituted benzyl group, g) di(p-methoxyphenyl)methyl, h) triphenylmethyl, i) (p-methoxyphenyl)diphenylmethyl, j) diphenyl-4-pyridylmethyl, k) 2,4,6-trimethylbenzenesulphonyl, l) toluenesulphonyl, m) benzylsulphonyl, n) a C$_{1-6}$ alkyl group, o) a trifluoro C$_{1-4}$ alkyl group, p) an alkynyl group or q) p-methoxybenzyl or unsubstituted or substituted ammonium.

3. A process according to claim 2 wherein R$_1$ represents benzyl.

4. A process according to claim 1 wherein the metal hydride is sodium hydride, potassium hydride, magnesium hydride, calcium hydride, sodium borohydride, potassium borohydride, lithium borohydride, lithium aluminium hydride, sodium aluminium hydride, aluminium hydride, sodium bis-(2-methoxyethoxy)aluminium hydride, a lithium mono(C$_{1-4}$ alkoxy)aluminium hydride, a lithium di(C$_{1-4}$ alkoxy)aluminium hydride or sodium diethylaluminium hydride or mixtures thereof.

5. A process according to claim 1 wherein the metal hydride is lithium aluminium hydride or sodium aluminium hydride.

6. A process according to claim 1 wherein the inorganic salt is a salt of lithium, sodium, magnesium, calcium, zinc, lanthanum or iron, or mixtures thereof.

7. A process according to claim 6 wherein the inorganic salt is a halide salt.

8. A process according to claim 7 wherein the inorganic salt is magnesium chloride, magnesium bromide or magnesium iodide.

9. A process according to claim 1 wherein the diluent is an ether or a hydrocarbon or a mixture thereof.

10. A process for producing paroxetine, in which
   a) the hydroxy group of a compound of formula I, prepared according to claim 1, is converted into a leaving group,
   b) the compound is reacted with sesamol or a salt thereof,
   c) the protecting group R$_1$ of the compound is removed, and optionally,
   d) the resulting compound is formed into a salt.

* * * * *